(12) United States Patent
Bertolero et al.

(10) Patent No.: US 7,682,305 B2
(45) Date of Patent: Mar. 23, 2010

(54) METHODS AND DEVICES FOR CARDIAC SURGERY

(75) Inventors: Art Bertolero, Danville, CA (US); Steve Geyster, Milton, MA (US)

(73) Assignee: Endoscopic Technologies, Inc., San Ramon, CA (US)

( * ) Notice: Subject to any disclaimer, the term of this patent is extended or adjusted under 35 U.S.C. 154(b) by 785 days.

(21) Appl. No.: 10/731,683

(22) Filed: Dec. 8, 2003

(65) Prior Publication Data

US 2005/0010079 A1    Jan. 13, 2005

Related U.S. Application Data

(60) Provisional application No. 60/431,628, filed on Dec. 6, 2002.

(51) Int. Cl.
*A61F 2/00* (2006.01)
(52) U.S. Cl. ........................................................ 600/37
(58) Field of Classification Search ............... 600/37, 600/16, 227–229, 201, 231–232, 235, 206, 600/210
See application file for complete search history.

(56) References Cited

U.S. PATENT DOCUMENTS

| 3,745,998 | A | 7/1973 | Rose |
| 4,224,929 | A | 9/1980 | Furihata |
| 4,445,892 | A | 5/1984 | Hussein et al. |
| 4,961,738 | A | 10/1990 | Mackin |
| 5,423,805 | A | 6/1995 | Brucker et al. |
| 5,503,617 | A | 4/1996 | Jako |
| 5,593,405 | A | 1/1997 | Osypka |
| 5,727,569 | A | 3/1998 | Benetti et al. |
| 5,782,746 | A | 7/1998 | Wright |
| 5,807,243 | A | 9/1998 | Vierra et al. |
| 5,836,311 | A | 11/1998 | Borst et al. |
| 5,865,730 | A | * | 2/1999 | Fox et al. ..................... 600/228 |
| 5,927,284 | A | 7/1999 | Borst et al. |
| 5,976,132 | A | 11/1999 | Morris |
| 6,013,027 | A | 1/2000 | Khan et al. |

(Continued)

OTHER PUBLICATIONS

Borst, Cornelius, et al., "Coronary artery bypass grafting without cardiopulmonary bypass and without interruption of native coronary flow using a novel anastomosis site restraining device ("Octopus")," JACC vol. 27, No. 6, May 1996, pp. 1356-1364.

(Continued)

*Primary Examiner*—Charles A Marmor, II
*Assistant Examiner*—Christine D Hopkins
(74) *Attorney, Agent, or Firm*—Townsend and Townsend and Crew LLP (57) ABSTRACT

Methods for performing minimally invasive heart surgery include accessing a heart of a patient through a first incision on the left thorax of the patient, contacting the heart through the incision with a heart stabilizing device and/or a heart positioning device, introducing at least one coupling device through a second incision on the patient located apart from the first incision, coupling the coupling device with the heart stabilizing device or the heart positioning device, and performing a surgical procedure on the heart. Systems may include a retractor device, a heart stabilizing device, and a coupling device, for enhancing cardiac surgery. Any suitable heart surgery may be performed using methods, devices or systems of the present invention. In one embodiment, a CABG procedure is performed.

20 Claims, 6 Drawing Sheets

U.S. PATENT DOCUMENTS

| | | | |
|---|---|---|---|
| 6,015,378 A | 1/2000 | Borst et al. | |
| 6,036,641 A | 3/2000 | Taylor et al. | |
| 6,036,685 A | 3/2000 | Mueller | |
| 6,039,733 A | 3/2000 | Buysse et al. | |
| 6,086,586 A | 7/2000 | Hooven | |
| 6,110,106 A | 8/2000 | MacKinnon et al. | |
| 6,161,543 A | 12/2000 | Cox et al. | |
| 6,237,605 B1 | 5/2001 | Vaska et al. | |
| 6,251,065 B1 | 6/2001 | Kochamba et al. | |
| 6,277,065 B1 | 8/2001 | Donofrio | |
| 6,309,349 B1 | 10/2001 | Bertolero et al. | |
| 6,328,688 B1 | 12/2001 | Borst et al. | |
| 6,334,843 B1 | 1/2002 | Borst et al. | |
| 6,336,898 B1 | 1/2002 | Borst et al. | |
| 6,338,712 B2 | 1/2002 | Spence et al. | |
| 6,338,738 B1 | 1/2002 | Bellotti et al. | |
| 6,346,077 B1 | 2/2002 | Taylor et al. | |
| 6,350,229 B1 | 2/2002 | Borst et al. | |
| 6,352,534 B1 | 3/2002 | Paddock et al. | |
| 6,364,826 B1 | 4/2002 | Borst et al. | |
| 6,371,906 B1 | 4/2002 | Borst et al. | |
| 6,390,976 B1 * | 5/2002 | Spence et al. | 600/210 |
| 6,394,948 B1 | 5/2002 | Borst et al. | |
| 6,463,332 B1 | 10/2002 | Aldrich | |
| 6,464,630 B1 | 10/2002 | Borst et al. | |
| 6,484,727 B1 | 11/2002 | Vaska et al. | |
| 6,511,416 B1 | 1/2003 | Green, II et al. | |
| 6,514,250 B1 | 2/2003 | Jahns et al. | |
| 6,522,905 B2 | 2/2003 | Desai | |
| 6,524,338 B1 | 2/2003 | Gundry | |
| 6,527,767 B2 | 3/2003 | Wang et al. | |
| 6,544,263 B2 | 4/2003 | Morgan et al. | |
| 6,595,989 B1 | 7/2003 | Schaer | |
| 6,599,237 B1 | 7/2003 | Singh | |
| 6,652,518 B2 | 11/2003 | Wellman et al. | |
| 6,758,809 B2 * | 7/2004 | Briscoe et al. | 600/229 |
| 6,849,075 B2 | 2/2005 | Bertolero et al. | |
| 7,226,448 B2 | 6/2007 | Bertolero et al. | |
| 7,237,555 B2 | 7/2007 | Kochamba et al. | |
| 7,338,434 B1 * | 3/2008 | Haarstad et al. | 600/37 |
| 2002/0026094 A1 | 2/2002 | Roth | |
| 2002/0056460 A1 | 5/2002 | Boyd | |
| 2002/0068855 A1 * | 6/2002 | Daniel et al. | 600/235 |
| 2002/0099270 A1 * | 7/2002 | Taylor et al. | 600/204 |
| 2002/0099390 A1 | 7/2002 | Kaplan | |
| 2002/0177846 A1 | 11/2002 | Mulier et al. | |
| 2003/0009080 A1 * | 1/2003 | Peng et al. | 600/37 |
| 2003/0010346 A1 * | 1/2003 | Paolitto et al. | 128/898 |
| 2003/0060685 A1 * | 3/2003 | Houser et al. | 600/206 |
| 2003/0158463 A1 * | 8/2003 | Julian et al. | 600/104 |
| 2003/0158464 A1 | 8/2003 | Bertolero | |
| 2005/0119653 A1 | 6/2005 | Swanson | |
| 2005/0119654 A1 | 6/2005 | Swanson et al. | |
| 2005/0240175 A1 | 10/2005 | Bertolero et al. | |
| 2006/0015165 A1 | 1/2006 | Bertolero et al. | |
| 2006/0155272 A1 | 7/2006 | Swanson | |
| 2007/0233226 A1 | 10/2007 | Kochamba et al. | |

OTHER PUBLICATIONS

Jansen, Erik, et al., "Less Invasive off-pump CABG using a suction device for immobilization: The Octopus method," European Journal of Cardiothoracic surgery 12 (1997) pp. 406-412.

* cited by examiner

METHODS AND DEVICES FOR CARDIAC SURGERY

CROSS-REFERENCE TO OTHER APPLICATIONS

This application claims priority of U.S. Provisional Application No. 60/431,628, filed Dec. 6, 2002, the specification of which is hereby incorporated by reference in its entirety.

FIELD OF THE INVENTION

The present invention relates generally to medical devices, systems and methods. More specifically, the device relates to devices, systems and methods for performing and/or enhancing heart surgery procedures.

BACKGROUND OF THE INVENTION

Heart disease continues to be the leading cause of death in the United States, with coronary artery disease (CAD) accounting for much of the mortality rate. As such, many interventional techniques have been developed to treat CAD, and surgeries to treat the disease are common. One commonly performed surgery, for example, is coronary artery bypass grafting (CABG), in which a graft, often from the internal mammary artery, is used to bypass an occluded coronary artery to supply blood to the heart.

Although CABG procedures are often quite successful, improvements in such procedures are continually being sought, to reduce patient morbidity and mortality and to improve outcomes. For example, a traditional technique for CABG surgery involves creating a large incision through a patient's sternum, as well as stopping the heart and placing the patient on a cardiopulmonary bypass machine. Many other types of heart surgery similarly require large incisions and cardiopulmonary bypass. Both of these components have significant potential for patient morbidity and increase the overall risk of cardiac surgical procedures. Thus, cardiac surgery techniques involving smaller incisions and/or techniques which can be performed on a beating heart have been developed.

Generally, certain drawbacks typically occur when heart surgery is attempted through smaller incisions. It is often difficult for a surgeon to establish adequate visualization of a heart, to be able to manipulate and use surgical instruments on the heart, to stabilize the position of the heart, and/or to move the heart to a more advantageous position through a relatively smaller incision. Basically, a smaller incision which does not allow a surgeon to split the patient's sternum and widely expose the left thoracic cavity may not allow the surgeon to manipulate the heart, perform the surgical procedure, and view the surgical field at the same time. If such inadequate access to the surgical site is compounded with the difficulty of operating on a moving, beating heart, results of a CABG procedure or other heart surgery will often suffer.

Therefore, it would be advantageous to have devices, systems and methods for enhancing the performance of heart surgery. For example, it would be advantageous to enable a surgeon to operate on a heart through a smaller incision than is conventionally used, while stabilizing and/or positioning the heart with one or more devices inserted through separate, minimally invasive incisions. Such methods, devices and systems would ideally be adaptable for either beating heart procedures or procedures on a stopped heart using cardiopulmonary bypass. At least some of these objectives will be met by the present invention.

BRIEF SUMMARY OF THE INVENTION

Devices, systems and methods of the present invention provide enhancement of heart surgery procedures. Generally, the invention provides for accessing a patient's heart through an incision on the left thorax, introducing a heart stabilizing device and/or a heart positioning device through the incision, introducing one or more coupling devices through separate incisions and coupling the coupling devices with the heart stabilizing device and/or the heart positioning device to stabilize and/or position the heart. Introducing one or more instruments through incisions that are separate from the main incision for accessing the heart provides open area for a surgeon to visualize the surgical field, insert additional instruments, manipulate instruments, manipulate the heart and/or the like. Embodiments of the invention may be used in either procedures involving a stopped heart and cardiopulmonary bypass or beating heart procedures.

In one aspect, a method of performing minimally invasive heart surgery includes: accessing a heart of a patient through a first incision on the left thorax of the patient; contacting the heart, through the incision, with at least one of a heart stabilizing device and a heart positioning device; introducing at least one coupling device through a second incision on the patient located apart from the first incision; coupling the at least one coupling device with at least one of the heart stabilizing device and the heart positioning device; and performing a surgical procedure on the heart. In some embodiments, for example, the first incision is located between two ribs of the patient. Optionally, accessing the heart includes Widening the first incision using at least one retractor device.

In some embodiments, the contacting step comprises contacting the heart with a heart stabilizing device and a heart positioning device. Optionally, such a method may further include using suction force to enhance contact of the heart stabilizing device and the heart positioning device with the heart. In some embodiments, the introducing and coupling steps involve introducing a first elongate coupling device through the second incision and coupling the first elongate coupling device with the heart stabilizing device. A method may further include introducing a second elongate coupling device through a third incision on the patient at a location apart from the first and second incisions and coupling the second elongate coupling device with the heart positioning device. In one embodiment, the method also includes coupling each of the first and second elongate coupling devices with at least one stabilizing apparatus for stabilizing the coupling devices. For example, coupling the coupling devices with the stabilizing apparatus may comprise coupling the first coupling device with a first stabilizing arm, coupling the second coupling device with a second stabilizing arm, and coupling the first and second stabilizing arms with at least one static object. The static object, for example, may comprise at least a portion of an operating room table. In some embodiments, the method may further include rigidifying the first and second stabilizing arms.

In some embodiments, the method may further comprise applying suction force with at least one of the heart stabilizing device and the heart positioning device to enhance contact between the device(s) and the heart. The surgical procedure itself may be any suitable procedure. For example, performing the surgical procedure may comprise performing a coronary artery bypass graft procedure.

In another aspect, a system for enhancing minimally invasive heart surgery comprises: at least one retractor device for enhancing access to a patient's heart through a first incision; a heart stabilizing device having a tissue contacting surface and at least one suction aperture adjacent the surface; and a first coupling device for coupling with the heart stabilizing device through a second incision at a location on the patient apart from the first incision. In some embodiments, the system will also comprise a heart positioning device having a tissue contacting surface and at least one suction aperture and a second coupling device for coupling with the heart positioning device through a third incision at a location on the patient apart from the first and second incisions.

The first and second coupling devices, in some embodiments, each comprise an elongate shaft having a proximal end, a distal end and means for coupling with the heart stabilizing device or the heart positioning device adjacent the distal end. The means for coupling, for example, may comprise a collet or socket for coupling with a ball on the heart stabilizing device or the heart positioning device. In such embodiments, the first and second coupling devices may further include a tightening device adjacent the proximal end of the shaft, for tightening the collet or socket around the ball. In other embodiments, the means for coupling comprises a clamp for coupling with the heart stabilizing device or the heart positioning device. In some embodiments, the elongate shaft comprises at least one flexible joint between the proximal end and the distal end. The flexible joint, for example, may comprise at least one collet or socket and ball joint.

Some embodiments of the system may suitably include a first flexible arm for coupling the first coupling device with at least one stable object and a second flexible arm for coupling the second coupling device with the stable object. In some embodiments, the first and second flexible arms may be rigidified after coupling the first and second coupling devices with the stable object. The stable object may include any suitable object. In one embodiment, part of an operating room table is used. In some embodiments, each of the first and second flexible arms comprises: an elongate arm having a proximal end, a distal end and at least one joint disposed between the proximal end and the distal end; means near the distal end for coupling the arm with a coupling device; means near the proximal end for coupling the arm with the stable object; and means for rigidifying the at least one joint of the arm. In some embodiments, the means near the distal end and the means near the proximal end each comprises a clamp.

In yet another embodiment, a device for enhancing minimally invasive heart surgery comprises a heart stabilizing member and an elongate coupling member having a proximal end, a distal end and means near the distal end for coupling with the heart stabilizing member. The heart stabilizing member, for example, may comprise at least one tissue contacting surface, at least one suction aperture for applying suction force to enhance contact between the tissue contacting surface and heart tissue, and at least one suction port for connecting with a source of suction. For example, the means for coupling with the heart stabilizing member may comprise a collet or socket for coupling with a ball on the heart stabilizing member. In another embodiment, the means for coupling with the heart stabilizing member comprises a clamp. The elongate coupling member optionally further includes at least one flexible joint between the proximal end and the distal end. The joint, for example, may comprise a collet or socket and ball joint. In other embodiments, the joint comprises multiple flexible beads.

In still another embodiment, a device for enhancing minimally invasive heart surgery comprises a heart positioning member and an elongate coupling member having a proximal end, a distal end and means near the distal end for coupling with the heart stabilizing member. The heart positioning member may comprise at least one tissue contacting surface, at least one suction aperture for applying suction force to enhance contact between the tissue contacting surface and heart tissue, and at least one suction port for connecting with a source of suction. Again, the means for coupling with the heart positioning member may comprise a collet or socket for coupling with a ball on the heart positioning member. Alternatively, the means for coupling may comprise threads for coupling with complementary threads on a device, a slot for coupling with a surface feature on the device, a clamp, or any other suitable means. As above, the elongate member may include one or more flexible joints.

In another aspect, a device for enhancing cardiac surgery comprises at least one inflatable tissue contacting surface, at least one port coupled with the tissue contacting surface for allowing inflation of the surface, and an elongate shaft defining a proximal end and a distal end, the shaft being removably couplable with the inflatable tissue contacting surface at or near the distal end. These and other embodiments are described in further detail below.

DETAILED DESCRIPTION OF THE INVENTION

Devices, systems and methods of the present invention provide for enhancement of heart surgery procedures. Generally, the invention provides for accessing a patient's heart through an incision on the left thorax, introducing a heart stabilizing device and/or a heart positioning device through the incision, introducing one or more coupling devices through one or more separate incisions and coupling the coupling device(s) with the heart stabilizing device and/or the heart positioning device to stabilize and/or position the heart. Introducing one or more instruments through incisions that are separate from the main incision for accessing the heart provides a less cluttered surgical field, to provide the surgeon with enhanced visualization and room to insert additional instruments, manipulate instruments, manipulate the heart, operate on the heart, perform an anastamosis and the like. Various embodiments of the invention may be used in procedures involving a stopped heart and cardiopulmonary bypass, partial bypass, or in beating heart procedures.

Generally, any suitable devices or combinations of devices may be used with methods of the present invention. One embodiment, for example, may employ one or more retractors as described in U.S. Pat. No. 6,309,349, entitled "Surgical Retractor and Stabilizing Device and Method for Use," the entire disclosure of which is hereby incorporated by reference. Some embodiments may include one or more of the following: heart stabilizing devices, such as those described in U.S. Utility application Ser. No. 10/297,791, a National Stage Application of PCT/US01/04263; heart positioning devices, such as those described in U.S. Provisional Patent Applications 60/491,323, filed Jul. 29, 2003 and 60/519,837, filed Nov. 11, 2003; heart ablation devices, such as those described in U.S. Provisional Patent Application 60/519,726, filed Nov. 12, 2003; instrument stabilizing platforms, such as those described in U.S. Provisional Patent Application No. 60/519,221, filed Nov. 11, 2003; and/or the like. The entire disclosures of these applications are hereby incorporated by reference.

Figure 1:
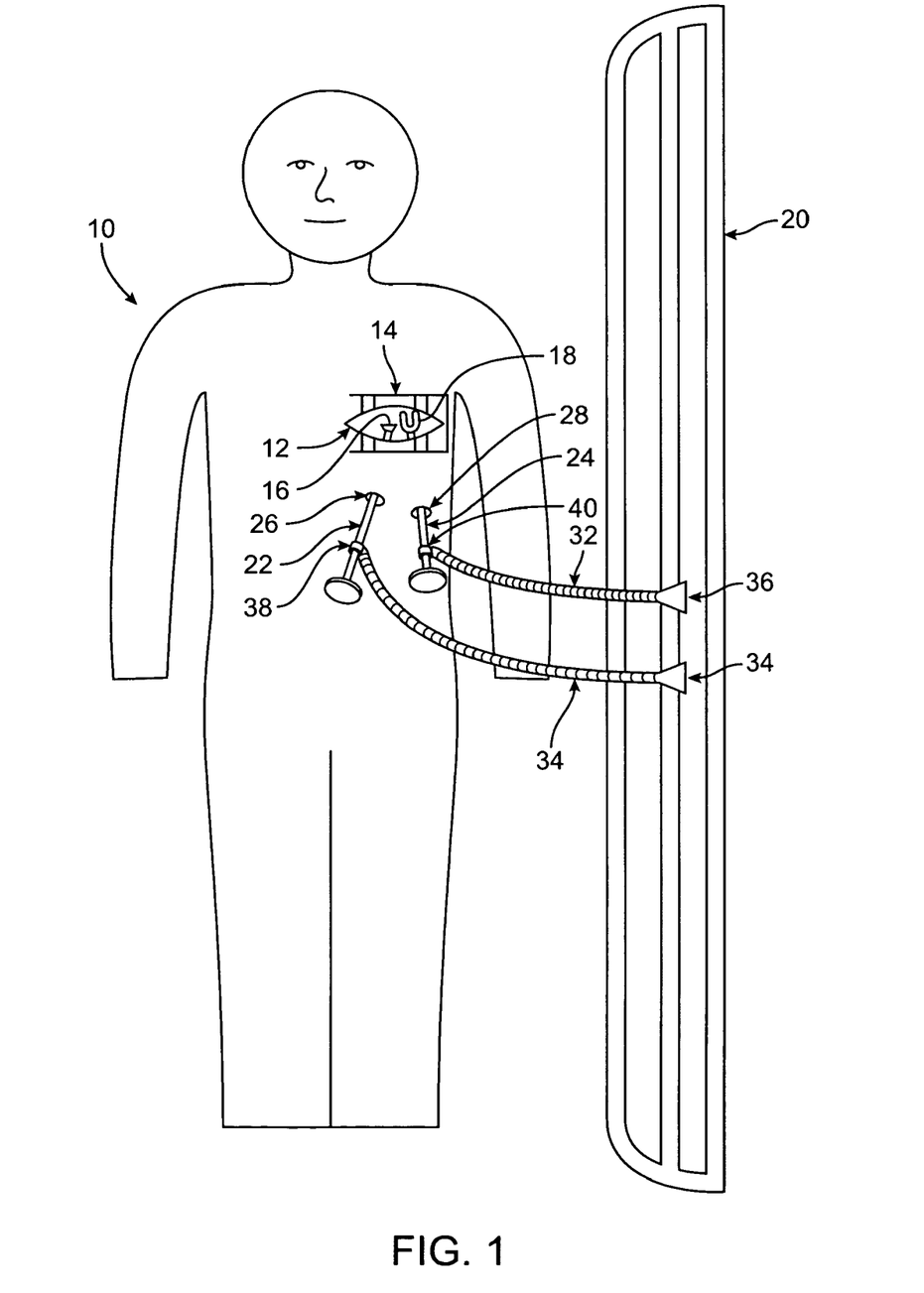
FIG. 1 is a perspective view of a patient with a system for performing a heart surgery in position on the patient, according to one embodiment of the present invention.

Referring now to FIG. 1, a schematic diagram of a patient 10 is shown adjacent a rail 20 of an operating room table, with a surgical system in position for enabling a heart surgery procedure. A surgical system may include, in one embodiment, a retractor device 14 for retracting skin and other tissues surrounding a thoracic incision 12 on patient 10. The system may also include a heart stabilizing device 18 and/or a heart positioning device 16, each of which may be coupled with a coupling device 22, 24. Each coupling device 22, 24 may, in turn, be coupled with a flexible arm 30, 32, and each arm may be coupled with a stable object, such as rail 20. The combination shown in FIG. 1 and described herein is only one embodiment of such a system, however, and should not be interpreted as limiting the scope of the invention. In various embodiments, many different combinations of surgical instruments, stabilizing devices, coupling devices, retractor devices and the like may be used, without departing from the scope of the invention. Generally, therefore, any system for performing heart surgery in which a device or part of a first device is introduced through a first incision and second device is introduced through a second, separate incision and coupled with the first device is contemplated within the scope of the invention.

Generally, any suitable thoracic incision 12 may be used in accordance with the present invention. For example, incision 12 may be made between the 4th and 5th ribs in one embodiment. Once incision 12 is formed, retractor device 14, or one or more alternative retractor devices, may be used to gain access to the patient's heart (not shown). In other embodiments, other access means may be used, such as any suitable incision(s), port(s), puncture site(s) or the like. Once the heart tissue is accessible, heart stabilizing device 18 and/or heart positioning device 16 are introduced through incision 12 and placed on the surface of the heart. The surgeon may then position the device(s) 16, 18 on the heart at or near a desired location, or may wait until a later time to position the device(s) 16, 18. Next, one or more small, secondary incisions 26, 28 are made at locations apart from thoracic incision 12, typically at nearby locations on the patient's thorax, but suitably in other locations as well. The incisions may be small, stab-wound incisions of less than one inch in length, in some embodiments. In some embodiments, as in FIG. 1, two small incisions 26, 28 are formed, to allow passage of two coupling devices 22, 24. Generally, any suitable incisions, ports, puncture sites, intravascular access sites, other access means or any combination thereof may be used.

A coupling device 22, 24, as described in further detail below, typically comprises an elongate shaft with means for coupling with stabilizing device 18 and/or positioning device 16 near the distal end of the shaft. Coupling device 22, 24, is introduced through a smaller incision 26, 28 and advanced through the patient, under the skin, to position the distal end of the shaft at or near the surgical site, adjacent the heart. The coupling means are then used to attach coupling device 22, 24 to stabilizing device 18 or positioning device 16. In various embodiments, multiple coupling devices 22, 24 may be introduced through one incision, heart stabilizing device 18 and heart positioning device 16 may be coupled with the same coupling device 22, 24, and/or additional heart contacting devices or coupling devices may be used without departing from the scope of the present invention. Any suitable combination of heart contacting devices and coupling devices is contemplated within the scope of the invention.

Once coupling devices 22, 24 are coupled with stabilizing device 18 and positioning device 16, coupling devices 22, 24 may be used to position stabilizing and positioning devices 18, 16 on the heart. Once in position, suction and/or other forces such as adhesives may be used to enhance contact between stabilizing and positioning devices 18, 16 and the heart. In embodiments using suction, a source of suction, such as a cannula, may be introduced through one of the smaller incisions 26, 28 or through the larger, thoracic incision 12, depending on convenience and preference of the surgeon. In either case, a suction cannula is typically connected with heart stabilizing device 18 or heart positioning device 16 directly, rather than through coupling devices 22, 24. In some embodiments, however, one or more suction cannulas may be attached to coupling device 22, 24, to facilitate introduction of the cannula to the surgical site, to reduce cluttering of the surgical site, or for any other suitable purpose.

When coupling devices 22, 24 have been coupled with heart stabilizing device 18 and heart positioning device 16 and the devices have been positioned on the heart and coupled with the heart via suction or other forces, each coupling devices 22, 24 may then be coupled with one or more stable objects via a flexible arm 32, 30. Flexible arms may comprise any suitable devices for stabilizing coupling devices 22, 24. For example, arms 32, 30 may comprise elongate, flexible members having distal clamps 38, 40 at their distal ends and proximal clamps 34, 36 at their proximal ends. Flexible arms 30, 32 may comprise metallic arms having multiple joints, to allow flexibility while also being rigid enough to stabilize coupling members. In another embodiment, flexible arms 30, 32 may be rigidifying, so that they may be manipulated into a desired position and then rigidified to hold their shape. In one embodiment, for example, arms 30, 32 may be rigidified by applying suction. Flexible arms 30, 32 may be coupled at or near their proximal ends, via proximal claims 34, 36 or other coupling components to any stable object or objects. In one embodiment, for example, the stable object comprises a bed rail 20, but any other suitable object may be used.

Any of the steps described above, as well as additional steps, may be performed in any suitable order, steps may be combined or eliminated, or the like, without departing from the scope of the present invention. For example, in one embodiment, thoracic incision 12 may be formed, smaller incision(s) 26, 28 may be formed, coupling devices 22, 24 may be advanced and then stabilizing device 18 and positioning device 16 may be placed into the surgical site and coupled with coupling devices 22, 24. In another embodiment, flexible arms 30, 32 may be coupled with coupling devices 22, 24 and with the stable object before being rigidified, while other combinations are possible in other embodiments. Furthermore, as mentioned above, additional or other devices than those described above may be used, fewer devices may be used or the like, without departing from the scope of the invention.

Figure 2:
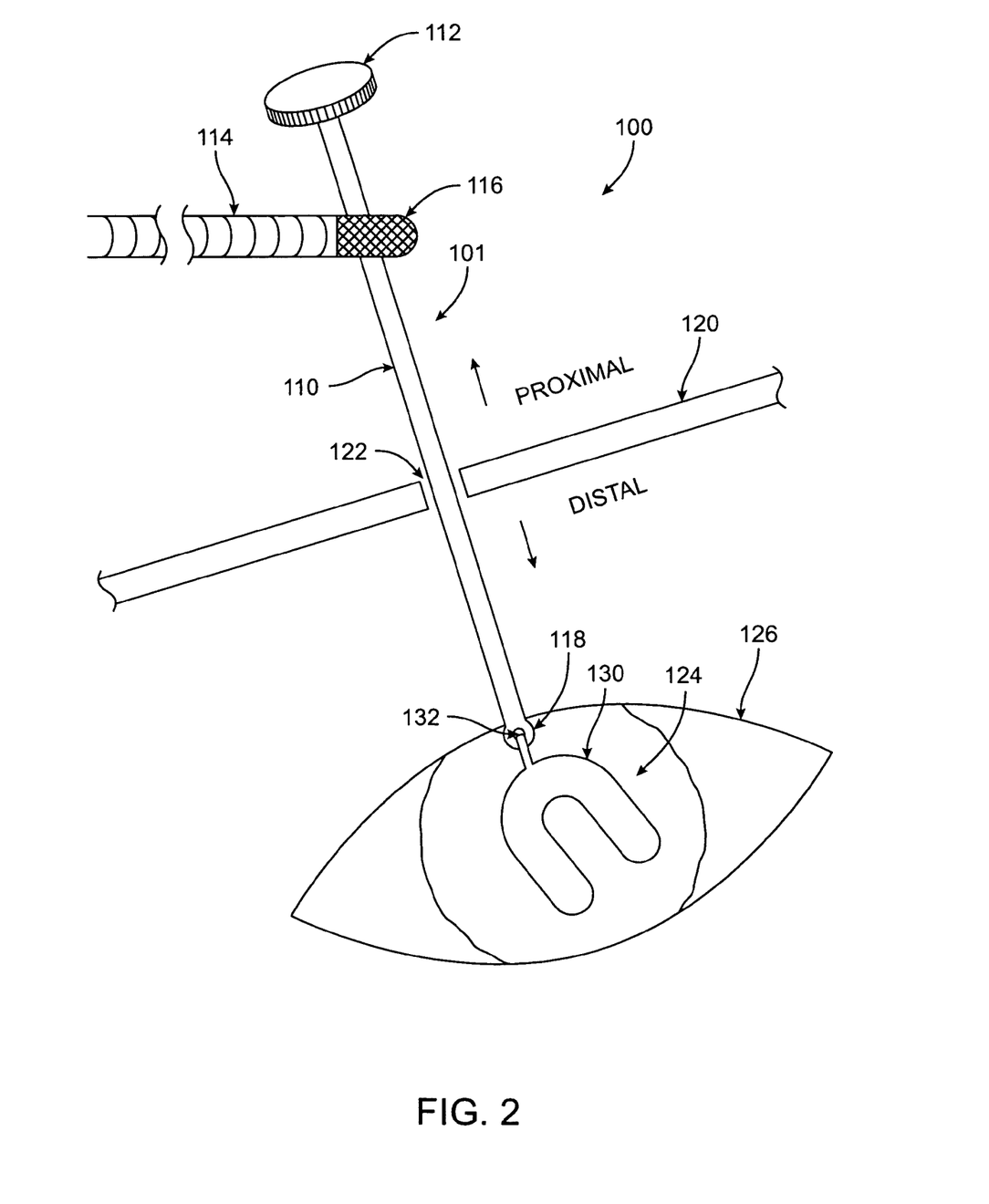
FIG. 2 is a perspective view of a device for enhancing heart surgery, according to one embodiment of the present invention.

With reference now to FIG. 2, a surgical apparatus 100 for enhancing heart surgery suitably includes a coupling device 101, coupled with a flexible arm 114 and a tissue stabilizing device 130 (or positioning device or other device). In one embodiment, coupling device 101 includes an elongate shaft 110 having proximal and distal ends (labeled arrows), which is coupled with a dial 112 or other actuation device at or near its proximal end and heart stabilization device 130 at or near its distal end. Flexible arm 114 generally comprises an elongate, flexible device with a clamp 116 at or near its distal end for coupling with coupling device 101. Clamp 116 may alternatively comprise any suitable connective means.

Elongate shaft 110 of coupling device 101 is generally introduced into a patient through a minimally invasive incision 122 in the skin 120, and is then advanced distally until the distal end of coupling device 101 is visible through a thoracic incision 126 over the heart 124. Elongate shaft 110 may have any suitable configuration. In some embodiments, shaft 110 includes one or more flexible, rigidifying sections. In some embodiments, such sections may rigidify by applying a vacuum to that section of shaft. Other embodiments may use different rigidifying means. Distal coupling means 118 at or near the distal end of coupling device 101 may then be coupled with heart stabilizing device 130 via complementary coupling means 132 on device 130. In one embodiment, distal coupling means 118 comprises a socket or collet and complementary coupling means 132 comprises a ball, or a ball on a post, which fits within distal coupling means 118. In another embodiment, distal coupling means 118 comprises a clamp and complementary coupling means 132 comprises a rail or other feature onto which the clamp make take hold. Any suitable combination allowing coupling device 101 to attach to heart stabilization device 130 is contemplated. Various embodiments may include, for example, a male and female screw connection, a magnetic connection, an adhesive connection, a snap-fit connection, a pressure-fit connection or the like. At or near the proximal end of coupling device 101, dial 112 may in fact comprise any actuation device, such as but not limited to a knob, trigger, slide or the like. Similarly, dial 112 may be used to perform any function or combination of functions with coupling device 101. For example, in one embodiment dial 112 is used to tighten and loosen distal coupling means 118 to allow coupling device 101 to be coupled with, tighten around and release heart stabilizing device 132. In other embodiments, dial 112 may control one or more alternative or additional functions. Once coupling device 101 is coupled with heart stabilizing device 130, it may be used to position stabilizing device on the heart in a desired location and orientation.

Figure 2A:
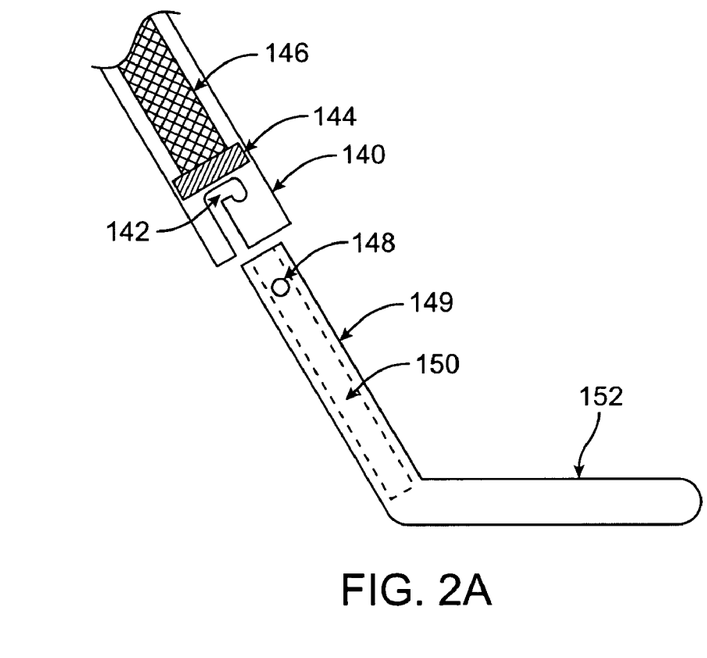
FIG. 2A is a perspective view of a distal end of a coupling device and a surgical instrument, according to one embodiment of the present invention.

With reference now to FIG. 2A, a coupling device distal end 140 is shown as an example of one embodiment of coupling means for coupling distal end 140 with a stabilizing device 149 or other suitable device. As previously mentioned, any suitable coupling means for connecting coupling device with a stabilization or other device is contemplated within the scope of the invention. Thus, a ball and socket joint, a ball and collet joint, any other suitable joint, an adhesive coupling means, a snap-fit or pressure fit coupling, or any other means may be used. For example, in yet another embodiment, as shown in FIG. 2A, distal end 140 includes a curved slot 142 and stabilizing device 149 includes a knob 148 which fits within slot 142 to provide coupling. In some embodiments, distal end 140 may also include a hollow lumen 146, such as a lumen for use in applying a vacuum force, and a gasket 144.

In some embodiments, stabilizing device 149 also includes a hollow lumen 150 such that when stabilizing device 149 and distal end 140 are coupled together, the two lumens 146, 150 are in fluid communication. This may allow vacuum, air, fluid and/or the like to be transmitted from the coupling device to the stabilizing device 149. Such vacuum, for example, may be used to adhere a supporting foot 152 of device 149 to a surface of the heart.

Figure 2B:
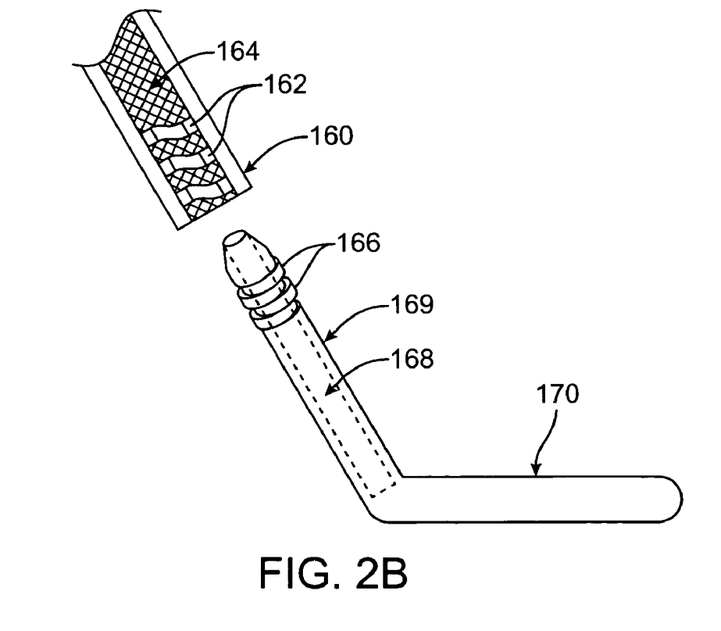
FIG. 2B is a perspective view of a distal end of a coupling device and a surgical instrument, according to another embodiment of the present invention.

In another embodiment, as shown in FIG. 2B, a distal end 160 of a coupling device may include female threads 162 which are complementary to male threads 166 on a stabilizing device 169 or other device. Again, distal end 160 may include a hollow lumen 164 and stabilizing device 169 may also include such a lumen 168 such that when they are coupled, the two lumens communicate. Again, one possible use of such communicating lumens 164, 168 might be to provide vacuum or suction force at a foot 170 of stabilizing device 169. Any other suitable configuration of distal ends, stabilizing devices (or other devices) and coupling means is contemplated within the scope of the invention. These examples are provided for descriptive purposes only and are not intended to limit the scope of the invention in any way.

Figure 3:
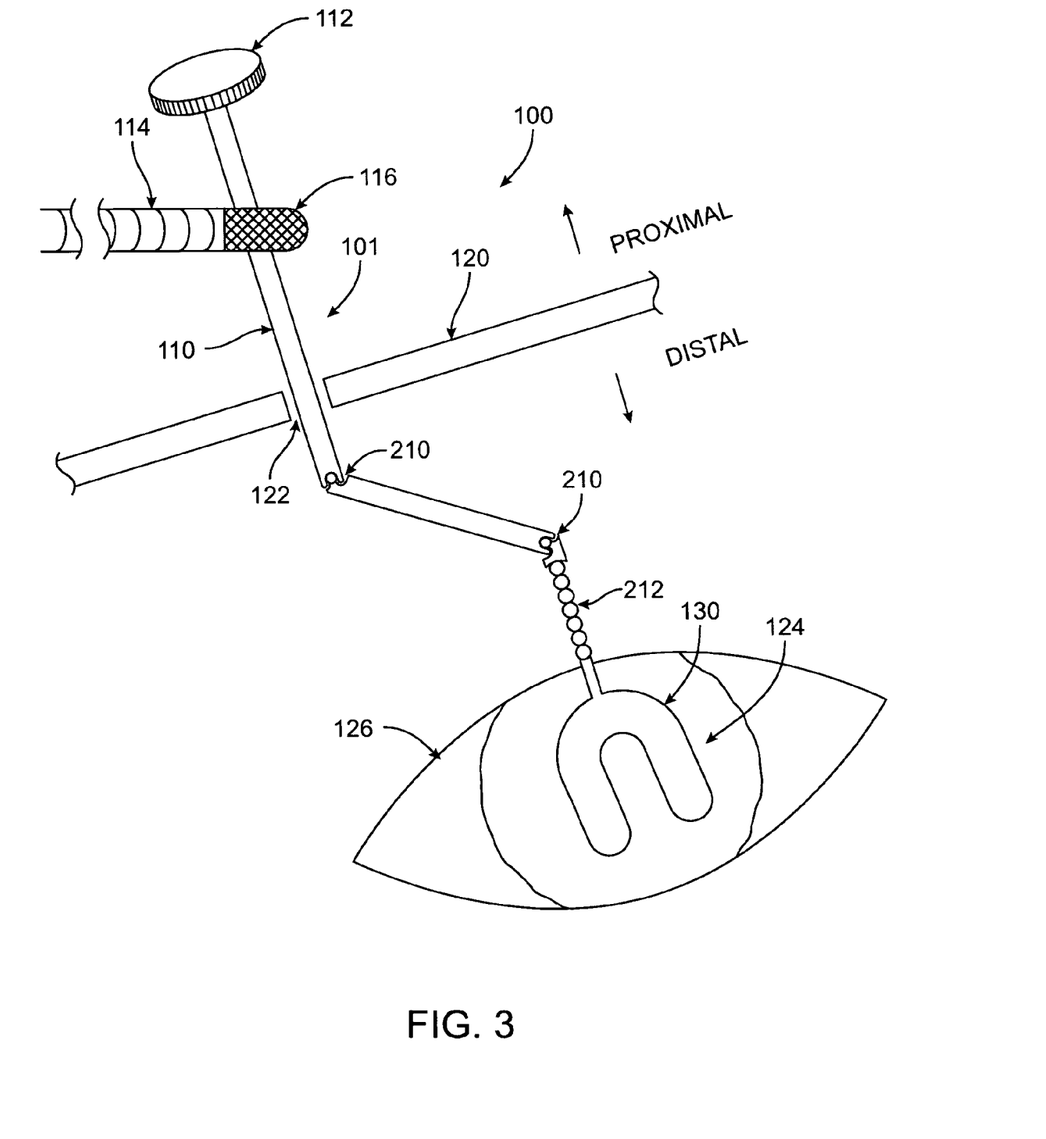
FIG. 3 is a perspective view of a device for enhancing heart surgery, according to another embodiment of the present invention.

Referring now to FIG. 3, a similar apparatus 100 to that described in FIG. 2 is shown. In this embodiment, however, elongate shaft 110 of coupling device 101 includes multiple, flexible joints 210. Flexible joints 210 may comprise ball and socket or ball and collet joints or may suitably include any other joint configuration. Joints 210 may provide coupling device 101 with enhanced flexibility and maneuverability within a patient to position the distal end of coupling device 101 in a desired location. Any number of joints 210 may be used and any position or combination of positions for joints 210 is contemplated. In some embodiments, dial 112 or one or more other actuators may be used to manipulate joints 210. For example, joints 210 in some embodiments may be moved via an actuator and/or may be tightened, to reduce flexibility once coupling device 101 is in a desired position. To further enhance flexibility of apparatus 100, a series of beads 212 or bearings may be incorporated into the distal end of coupling device 101, into heart stabilizing device 130 or both. Any such flexible components may be used.

Figure 4A:
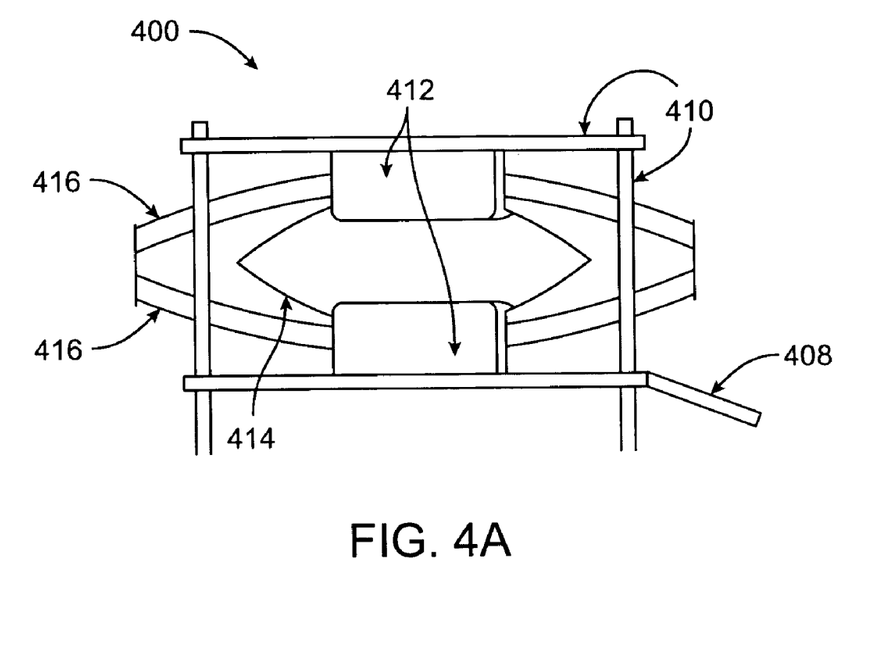
FIG. 4A is a top perspective view of a retractor positioned to retract an incision, according to one embodiment of the present invention.

With reference now to FIG. 4A, a retractor device 400 for use in systems and methods of the present invention suitably includes a frame 410, two or more retractor blades 412 coupled with frame 410, and a crank 408 or other actuator coupled with frame 410. Frame 410 may include two vertical rods and two horizontal rods that are slidably coupled with the vertical rods. Crank 408 may be used to move the horizontal rods relative to the vertical rods, to thus increase the distance by which blades 412 are separated and expand the width of an incision 414. Blades 412 may comprise any suitable retractor blades and any number and size of blades 412 may be used. In some embodiments, retractor device 400 will be configured to assist in separating ribs 416 as well as incision 414. Again, any number, configuration, size and the like of blades 412 may be used, and frame 412 may have any suitable shape, size and configuration. In some embodiments, only two or more blades may be used, without frame 410.

Figure 4B:
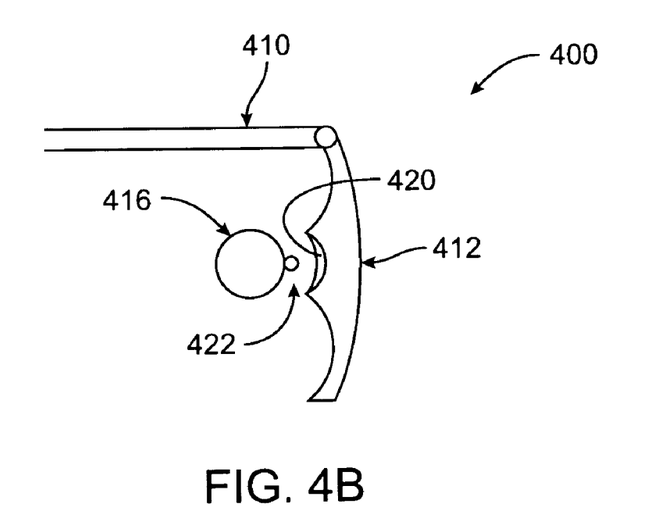
FIG. 4B is a side view of an improved retractor blade, according to one embodiment of the present invention.

Turning now to FIG. 4B, a side view of a portion of retractor device 400 is shown. In one embodiment, blade 412 includes a nerve protector 420 or detent. Nerve protector 420 is generally configured to apply pressure against rib 416, without damaging an intercostal nerve 422 associated with rib 416. As such, nerve protector 420 may have any suitable configuration and, in some embodiments, may include a soft or padded material, to allow blade 412 to adequately retract tissue and apply pressure against rib 416 without harming or damaging nerve 422.

More generally, any retraction device or combination of retraction devices may be included as part of a system or method according to the present invention. In one embodiment, for example, an inflatable retractor may be used. For example, two blades of a retractor may be coupled to one another at opposite ends and may be inflated to allow a portion of each blade to expand, pushing the blades apart between their connected ends. In other embodiments, any combination of conventional retractors or retractors not yet conceived may be used.

Similarly, any heart stabilizing device, heart positioning device and/or any other device may be used as part of a system or method of the invention. As mentioned above, one heart stabilizing device may comprise the OPVAC® heart stabilizer (available from Estech, Inc., www.estechlics.com, the entire contents of said web site being hereby incorporated by reference). The heart positioning device may comprise the Pyramid Positioner™ device (also available from Estech, Inc.). Alternatively, any other suitable devices may be used. Thus, the present invention is not limited to heart stabilizing devices and/or heart positioning devices.

Figure 5:
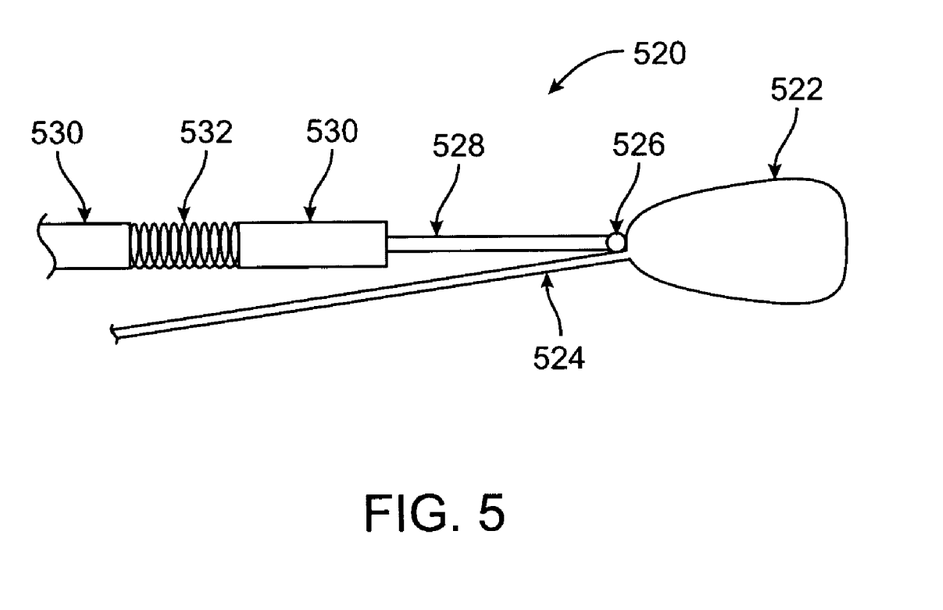
FIG. 5 is a perspective view of an inflatable heart positioning device, according to one embodiment of the present invention.

In one embodiment, an with reference now to FIG. 5, a stabilizing and/or positioning device comprises an inflatable heart retractor 520 or "pillow retractor." Inflatable retractor 520 comprises an inflatable retractor surface 522, coupled with an elongate shaft 528 via a flexible connector 526. Again, shaft 528 is coupled with a rapid disconnect 530, which may or may not include a flexible segment 532. Inflatable retractor 520 also includes means for inflating the retractor surface 522, which may comprise, for example, an inflation cannula 524 within or outside of elongate shaft 528. Inflatable heart retractor 520 may be particularly advantageous in positioning the heart by placing the inflatable surface 522 in contact with a posterior portion of the heart and inflating the surface 522 to move the heart in an anterior direction—i.e., closer to the surgeon. Many alternate embodiments of inflatable retractor 520 may be developed within the scope of the present invention. Creating a space behind the heart may be very advantageous in visualizing the back of the heart and/or in maneuvering one or more surgical devices to operate on the back of the heart. Other variations of inflatable retractors may be found in U.S. Provisional Application No. 60/519,512, filed Nov. 12, 2003, the entire disclosure of which is hereby incorporated by reference.

Although the invention has been fully described above, in relation to various exemplary embodiments, various additions or other changes may be made to the described embodiments without departing from the scope of the present invention. Thus, the foregoing description has been provided for exemplary purposes only and should not be interpreted to limit the scope of the invention as set forth in the following claims.

What is claimed is:

1. A system for enhancing minimally invasive heart surgery, the system comprising:

at least one retractor device for enhancing access to a patient's heart through a first incision;

a heart stabilizing device having a tissue contacting surface and at least one suction aperture adjacent the surface;

a first coupling device for coupling with the heart stabilizing device through a second incision at a location on the patient apart from the first incision, the first coupling device comprising:

an elongate shaft having a proximal end, a distal end, and at least one flexible, rigidifying portion comprising a plurality of pieces and a wire that when tightened locks the pieces of the rigidifying portion into place; and means for coupling the elongate shaft with the heart stabilizing device adjacent the distal end of the elongate shaft;

a first flexible arm for coupling the first coupling device with at least one stable object, wherein the first flexible arm comprises a distal clamp configured to clamp the first coupling device, and a proximal clamp configured to clamp the at least one stable object;

a heart positioning device having a tissue contacting surface and at least one suction aperture; and a second coupling device for coupling with the heart positioning device through a third incision at a location on the patient apart from the first and second incisions.

2. A system as in claim 1, wherein the second coupling device comprises an elongate shaft having a proximal end, a distal end, and at least one flexible, rigidifying portion comprising a plurality of pieces and a wire that when tightened locks the pieces of the rigidifying portion into place, and means for coupling the elongate shaft with the heart positioning device adjacent the distal end of the elongate shaft.

3. A system as in claim 2, wherein the means for coupling the elongate shaft of the first coupling device comprises a collet or socket for coupling with a ball on the heart stabilizing device, and the means for coupling the elongate shaft of the second coupling device comprises a collet or socket for coupling with a ball on or the heart positioning device.

4. A system as in claim 3, wherein each of the first and second coupling devices further include a tightening device adjacent the proximal end of the elongate shaft, for tightening the collet or socket around the ball.

5. A system as in claim 2, wherein the means for coupling the elongate shaft of the first coupling device with the heart stabilizing device comprises a slot for coupling with a surface feature on the heart stabilizing device or the means for coupling the elongate shaft of the second coupling device with the heart positioning device comprises a slot for coupling with a surface feature on the heart positioning device.

6. A system as in claim 2, wherein the means for coupling the elongate shaft of the first coupling device with the heart stabilizing device comprises threads for coupling with complementary threads on the heart stabilizing device or the means for coupling the elongate shaft of the second coupling device with the heart positioning device comprises threads for coupling with complementary threads on the heart positioning device.

7. A system as in claim 2, wherein the means for coupling the elongate shaft of the first coupling device with the heart stabilizing device comprises a clamp for coupling with the heart stabilizing device or the means for coupling the elongate shaft of the second coupling device with the heart positioning device comprises a clamp for coupling with the heart positioning device.

8. A system as in claim 2, wherein the elongate shaft of the first coupling device comprises at least one flexible joint between the proximal end and the distal end of the elongate shaft of the first coupling device or the elongate shaft of the second coupling device comprises at least one flexible joint between the proximal end and the distal end of the elongate shaft of the second coupling device.

9. A system as in claim 8, wherein the at least one flexible joint comprises at least one collet or socket and ball joint.

10. A system as in claim 1, further comprising:
a second flexible arm for coupling the second coupling device with the at least one stable object.

11. A system as in claim 10, wherein the first and second flexible arms may be rigidified after coupling the first and second coupling devices with the stable object.

12. A system as in claim 10, wherein the at least one stable object comprises at least one part of an operating room table.

13. A system as in claim 10, wherein each of the first and second flexible arms comprises:
an elongate arm having a proximal end, a distal end and at least one joint disposed between the proximal end and the distal end;
means near the distal end of the elongate arm for coupling the elongate arm with a coupling device;
means near the proximal end of the elongate arm for coupling the elongate arm with the stable object; and
means for rigidifying the at least one joint of the elongate arm.

14. A system as in claim 13, wherein the means near the distal end of the elongate arm and the means near the proximal end of the elongate arm each comprises a clamp.

15. A system for enhancing minimally invasive heart surgery, the system comprising:
at least one retractor device for enhancing access to a patient's heart through a first incision;
a heart stabilizing device having a tissue contacting surface and at least one suction aperture adjacent the surface;
a first coupling device for coupling with the heart stabilizing device through a second incision at a location on the patient apart from the first incision, the first coupling device comprising:
an elongate shaft having a proximal end, a distal end, and at least one flexible, rigidifying portion comprising a plurality of pieces and a wire that when tightened locks the pieces of the rigidifying portion into place; and
means for coupling the elongate shaft with the heart stabilizing device adjacent the distal end of the elongate shaft; and
a first flexible arm for coupling the first coupling device with at least one stable object, wherein the first flexible arm comprises a distal clamp configured to clamp the first coupling device, and a proximal clamp configured to clamp the at least one stable object,
wherein the at least one retractor device comprises:
a retractor frame for movably holding at least two retractor blades;
at least two retractor blades coupled with the retractor frame, for retracting tissue adjacent an incision; and
means for moving the retractor frame so as to move the blades to retract the tissue.

16. A system as in claim 15, wherein each of the at least two retractor blades includes nerve protection means for inhibiting damage to an intercostal nerve when retracting a rib.

17. A system as in claim 15, wherein the means for moving the retractor frame comprises a crank handle.

18. A system for enhancing minimally invasive heart surgery, the system comprising:
at least one retractor device for enhancing access to a patient's heart through a first incision;
a heart stabilizing device having a tissue contacting surface and at least one suction aperture adjacent the surface;
a first coupling device for coupling with the heart stabilizing device through a second incision at a location on the patient apart from the first incision, the first coupling device comprising:
an elongate shaft having a proximal end, a distal end, and at least one flexible, rigidifying portion comprising a plurality of pieces and a wire that when tightened locks the pieces of the rigidifying portion into place; and
means for coupling the elongate shaft with the heart stabilizing device adjacent the distal end of the elongate shaft; and
a first flexible arm for coupling the first coupling device with at least one stable object, wherein the first flexible arm comprises a distal clamp configured to clamp the first coupling device, and a proximal clamp configured to clamp the at least one stable object,
wherein the heart stabilizing device comprises:
at least one tissue contacting surface;
at least one suction aperture for applying suction force to enhance contact between the tissue contacting surface and heart tissue; and
at least one suction port for connecting with a source of suction.

19. A system for enhancing minimally invasive heart surgery, the system comprising:
at least one retractor device for enhancing access to a patient's heart through a first Incision;
a heart stabilizing device having a tissue contacting surface and at least one suction aperture adjacent the surface;
a first coupling device for coupling with the heart stabilizing device through a second incision at a location on the patient apart from the first incision, the first coupling device comprising:
an elongate shaft having a proximal end, a distal end, and at least one flexible, rigidifying portion comprising a plurality of pieces and a wire that when tightened locks the pieces of the rigidifying portion into place; and
means for coupling the elongate shaft with the heart stabilizing device adjacent the distal end of the elongate shaft; and
a first flexible arm for coupling the first coupling device with at least one stable object, wherein the first flexible arm comprises a distal clamp configured to clamp the first coupling device, and a proximal clamp configured to clamp the at least one stable object,
an actuation device coupled with the first coupling device, and
a distal coupling means that couples the coupling device with the heart stabilizing device,
wherein the actuation device can tighten and loosen the distal coupling means.

20. A system for enhancing minimally invasive heart surgery, the system comprising:
at least one retractor device for enhancing access to a patient's heart through a first incision;
a heart stabilizing device having a tissue contacting surface and at least one suction aperture adjacent the surface;
a first coupling device for coupling with the heart stabilizing device through a second incision at a location on the patient apart from the first incision, the first coupling device comprising:
an elongate shaft having a proximal end, a distal end, and at least one flexible, rigidifying portion comprising a plurality of pieces and a wire that when tightened locks the pieces of the rigidifying portion into place; and
means for coupling the elongate shaft with the heart stabilizing device adjacent the distal end of the elongate shaft; and a first flexible arm for coupling the first coupling device with at least one stable object, wherein the first flexible arm comprises a distal clamp configured to clamp the first coupling device, and a proximal clamp configured to clamp the at least one stable object, wherein the plurality of pieces comprises a plurality of beads.

* * * * *